(12) United States Patent
Strauss et al.

(10) Patent No.: US 6,392,076 B1
(45) Date of Patent: *May 21, 2002

(54) WEAKLY COORDINATING ANIONS CONTAINING POLYFLUOROALKOXIDE LIGANDS

(75) Inventors: Steven H. Strauss, Fort Collins; Benjamin P. Fauber, Arvada; Benjamin G. Nolan, Fort Collins, all of CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/523,502

(22) Filed: Mar. 10, 2000

Related U.S. Application Data

(60) Provisional application No. 60/123,599, filed on Mar. 10, 1999.

(51) Int. Cl.[7] .................................................. C08K 5/00
(52) U.S. Cl. ........................................ 556/40; 524/176
(58) Field of Search .............................. 524/176; 556/40

(56) References Cited

U.S. PATENT DOCUMENTS

| | | | |
|---|---|---|---|
| 5,534,370 A | 7/1996 | Kita et al. | 429/198 |
| 5,660,947 A | 8/1997 | Wuhr | 429/192 |
| 6,221,941 B1 * | 4/2001 | Strauss et al. | 524/176 |

FOREIGN PATENT DOCUMENTS

| | | |
|---|---|---|
| WO | WO 96/26967 | 9/1996 |
| WO | WO 00/20472 | 4/2000 |

OTHER PUBLICATIONS

Barbarich et al., "Coordination of the new weakly coordinating anions $Al(OCH(CF_3)_2)_4^-$, $Al(OC(CH_3(CF_3)_2)_4^-$, and $Al(OC(Ph(CF_3)_2)_4$ to the monovalent metal ions $Li^+$ and $Tl^+$," *Journal of Molecular Catalysis A: Chemical*, v. 128, 1998, pp. 289–331.

Rockwell et al., "$Nb(OCH(CF_3)_2)_6^-$: Prototype for a New Class of Weakly Coordinating Anions Based on Polyfluoroalkoxide substituents," *Inorg. Chimica Acta*, v. 263, 1997, pp. 195–200.

Samuels et el., "Organofluorine Binding to Sodium and Thallium (I) in Molecular Fluoroalkoxide Compounds,". *J. Am. Chem. Soc.*, v. 115, 1993, pp. 5093–5104.

Perozzi et al., "Directed Dilithiation of Hexafluorocumyl Alcohols—Formation of a Reagent for the Facile Introduction of a Stabilizing Bidentate Ligand in Compounds of Hypervalent Sulfur (10–S–4), Phosphorus (10–P–5), Silicon (10–Si–5), and Iodine (10–I–3)," *The Journal of Organic Chemistry*, v. 46, 1981, pp. 1049–1053.

Denmark et al., "Synthesis, Structure, and Reactivity of an Organogermanium Lewis Acid," *Organometallics*, v. 9, 1990, pp. 3015–3019.

Akiba et al., "First Example of Thermally Stable Hypervalent Bismuth Ate Complex (12–Bi–6) with Two Bidentate Ligands: Synthesis and Structure," *Tet. Lett.*, v. 30, 1989, pp. 953–956.

Laurent et al., "Synthesis and Characterization of Volatile Sodium Yttrium Fluoroalkoxides. Structure of $Na_3(OCH(CF_3)_2)_6(THF)_3$ and $Na_2Y(OCMe(CF_3)_2)_5(THF)_3$," *Inorg. Chem*, v. 34, 1995, 34, pp. 3980–3985.

Samuels et al., "Chemical Vapor Deposition of Metal Fluorides using Sodium and Zirconium Fluoroakloxides," *Chem. Mater.*, v. 6, 1994, pp. 1684–1692.

Yamamoto et al., "Synthesis and Structure of Six–Coordinated Organobismuth Compounds with Bidentate Ligands (12–Bi–6)," *Organometallics*, v. 12, 1993, pp. 3297–3303.

Samuels et al., "Structure/Volatility Correlation of Sodium and Zirconium Fluoroalkoxides," *Chem. Mater.*, v.7, 1995, pp. 929–935.

Allan et al., "Fully fluorinated alkoxides, Part IV. Derivatives of perfluoropinacol," *Canadian Journal of Chemistry*, v. 46, 1968, pp. 3671–3677.

Barthel et al., "A New Class of Electrochemically and Thermally Stable Lithium Salts for Lithium Battery Electrolytes: II. Conductivity of Lithium Organoborates in Dimethoxyethane and Propylene Carbonate," *J. Electrochem. Soc.*, v. 143, 1996, pp. 3565–3571.

Barthel et al., "A New Class of Electrochemically and Thermally Stable Lithium Salts for Lithium Battery Electrolytes: III. Synthesis and Properties of Some Lithium Organoborates," *J. Electrochem. Soc.* v. 143, 1996, pp. 3572–3575.

Barthel et al., "A New Class of Electrochemically and Thermally Stable Lithium Salts for Lithium Battery Electrolytes: IV. Investigations of the Electrochemical Oxidation of Lithium Organobortes," *J. Electrochem. Soc.*, v. 144, 1997, pp. 3866–3868.

Barthel et al., "Lithium Bis [5–fluoro–2–olato–1–benzenesulfonato (2–)–0,0']borate(1–), a New Anodically and Cathodically Stable Salt for Electrolytes of Lithium–Ion Cells,". *J. Electrochem. Soc.*, v. 145, 1998, pp. L17–L20.

Lee et al., "The Synthesis of a New Family of Boron–Based Anion Receptors and the study of Their Effect on Ion Pair Dissociation and Conductivity of Lithium Salts in Nonaqueous Solutions," *J. Electrochem Soc.*, v. 145, 1998, pp. 2813–2818.

(List continued on next page.)

Primary Examiner—Edward J. Cain
(74) Attorney, Agent, or Firm—Townsend and Townsend and Crew LLP

(57) ABSTRACT

A compound comprising a polyfluorinated anion and the use thereof is provided. Specifically, the present invention provides a compound comprising an anion which comprises a polyfluorinated alkoxide coordinated to a transition metal, or a Group III, IV or V element.

29 Claims, No Drawings

OTHER PUBLICATIONS

Barbarich et al., "LiAl(OC(Ph)(CF$_3$)$_2$)$_4$: A Hydrocarbon-Soluble Catalyst for Carbon–Carbon Bond–Forming Reactions," *Organometallics*, v. 15, 1996, pp. 3776–3778.

Purdy et al., New Alkoxides of Copper and the Alkaline and AlkaLine–Earth Metals. Crystal Structure of Na$_2$CU [OCH(CF$_3$)$_2$]$_4$, *Inorg. Chem*, v. 30, 1991, pp. 2812–2819.

Purdy and George, "Volatile Copper and /Barium–Copper Alkoxides. Crystal Structure of a Tricoordinate Copper (II) Complex, Ba(CU[OCMe(CF$_3$)$_2$]$_3$) $_2$," *Inorg. Chem*, v. 30, 1991, pp. 1969–1970.

Labrize and Hubert–Pfalzgraf, "Synthesis, Characterization and Reactivity of Volatile Yttrium–Sodium Fluoroisopropoxide Derivatives. Retention of Sodium as a General Feature," *Polyhedron*, v. 14, 1995, pp. 881–888.

Purdy and George, "Recent Developments in the Chemistry of Fluorinated Isopropoxides and Tertiary Butoxides," *Inorganic Fluorine Chemistry: Toward the 21$^{st}$ Century*, Chapter 26, 1994, pp. 405–420.

Willis, "Fluorinated Alcohols and Their Metal Complexes," *Coordination Chemistry Reviews*, v. 88, 1988, pp. 133–202.

* cited by examiner

WEAKLY COORDINATING ANIONS CONTAINING POLYFLUOROALKOXIDE LIGANDS

CROSS-REFERENCE TO RELATED APPLICATIONS

This application claims the benefit of U.S. Provisional Application No. 60/123,599, filed Mar. 10, 1999.

This application is also related to, but does not claim priority from, U.S. patent application Ser. No. 09/151,852, filed Sep. 11, 1998, which claims priority based on U.S. Provisional Patent Application Ser. No. 60/058,524, filed Sep. 11, 1997, disclosures of which are incorporated herein by reference in their entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. CHE-9628769 awarded by National Science Foundation.

FIELD OF THE INVENTION

The present invention relates to a compound containing polyfluoroalkoxides and the use thereof, in particular, for use as an electrolyte in batteries and other electrochemical devices.

BACKGROUND OF THE INVENTION

A compound containing a weakly coordinating anion (i.e., an anion that coordinates only weakly with a cation) is useful in a variety of applications including as an electrolyte and a counter-ion for a catalyst in a variety of organic reactions. Some of the useful catalysts containing a weakly coordinating anion are described by Barbarich, et al. in "LiAl(OC(Ph)(CF$_3$)$_2$)$_4$: A Hydrocarbon-Soluble Catalyst For Carbon-Carbon Bond-Forming Reactions", *Organometallics*, 1996, 15, 3776, which is incorporated herein in its entirety.

Investigations of very reactive metal and nonmetal cations continues to spur the development of new weakly coordinating anions. See, for example, Bochmann, *Angew. Chem., Int. Ed. Engl.* 1992, 31 1181; Strauss, *Chem. Rev.* 1993, 93, 927, Strauss, *Chemtracts-Inorganic Chem.* 1994, 6,1; and Seppelt, *Angew. Chem., Int. Ed. Engl.* 1993, 32, 1025. One of the most important uses of weakly coordinating anions is to enhance the catalytic activity of metal cations. Two examples that have received considerable attention recently are metallocene-catalyzed olefin polymerization, and lithium-catalyzed Diels-Alder reactions and 1,4-conjugate addition reactions. See Turner, European Patent Appl. No. 277,004, 1988; Pellecchia et al., *Makromol. Chem., Rapid Commun.* 1992, 13, 265; DuBay et al., *J. Org. Chem.* 1994, 59, 6898; Saidi et al., *Chem. Ber.* 1994, 127, 1761; Kobayashi et al., *Chem. Lett.* 1995, 307; and Arai et al., *Angew. Chem., Int. Ed. Engl.* 1996, 15, 3776.

Useful anions must not only be weakly coordinating, they must also be stable with respect to oxidation and/or fragmentation in the presence of highly electrophilic cations. In addition, an ideal weakly coordinating anion should have a single negative charge dispersed over a large surface composed of relatively nonpolar bonds to weakly basic atoms such as hydrogen or the halogens. Weakly coordinating anions which conform to many, but not all, of these criteria include B(Ar$_f$)$_4^-$ (Ar$_f$=C$_6$F$_5$ or 3,5-C$_6$H$_3$(CF$_3$)$_2$), CB$_{11}$H$_{12-n}$X$_n^-$ (X=H, Me, Cl, Br, F or I), CB$_9$H$_{10-n}$X$_n^-$ (X=H, F, Cl, or Br), and M(OTeF$_5$)$_n^-$ (n=4, M=B; n=6, M=Nb, Sb).

All of the anions mentioned above have limitations. Some are too strongly coordinating for specific applications. Some are unstable under the harsh chemical conditions where they would be employed. For example, the fluorinated derivatives of BPh$_4^-$ can react with strongly electrophilic cations, causing (i) cleavage of a C—F bond and formation of a bond between the fluorine atom and the cation or (ii) transfer of a fluoroaryl group to the cation. In either case, the cation is no longer reactive or catalytically active.

Other weakly coordinating anions, such as ClO$_4^-$, BF$_4^-$, PF$_6^-$, SbF$_6^-$, B(OTeF$_5$)$_4^-$, and Nb(OTeF$_5$)$_6^-$, are not thermally and/or hydrolytically stable. In addition, lithium salts of such anions, including LiCF$_3$SO$_3$, have low electrical conductivity in some organic solvents, especially organic solvents that are stable in the presence of strong reducing agents such as metallic lithium and related lithium-containing battery anode solutions. Furthermore, some lithium salts, such as lithium triflate (LiCF$_3$SO$_3$), cause corrosion of the aluminum current collectors in batteries, while some lithium salts, such as LiPF$_6$, are known to be unstable at temperatures as low as 70° C. and decompose over time.

Still other anions containing boron atoms, and anions containing a carbon atom and a cluster of boron atoms, such as carboranes (e.g., CB$_5$, CB$_9$, CB$_{11}$), are not particularly weakly coordinating because the salts formed therefrom contain at most only one fluorine atom which is bonded to a boron atom.

Recently, polyfluorinated carborane anions that are weakly coordinating and are thermally and/or hydrolytically stable have been disclosed in commonly assigned U.S. patent application Ser. No. 09/049,420, filed Mar. 27, 1998. In addition, one particular class of compounds containing polyfluoroalkoxide ligands and the use thereof has been disclosed in commonly assigned PCT Patent Application No. PCT/US98/19268, filed Sep. 11, 1998, and commonly assigned U.S. patent application Ser. No. 09/151,852, filed Sep. 11, 1998, disclosures of which are incorporated herein by reference in their entirety.

Despite the recent advances in weakly coordinating anions, there still is a need for new weakly coordinating anions. There is also a need for weakly coordinating anions having a high electrical conductivity in an organic solvent. There is also a need for weakly coordinating anions that are stable in solution and in the solid state.

SUMMARY OF THE INVENTION

One embodiment of the present invention provides a compound comprising a monoanion of the formula:

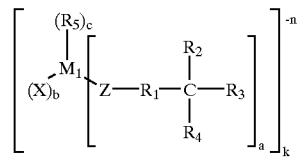

and uses thereof,
where
  M$_1$ is a transition metal, or a Group III, IV or V element;
  each Z is independently O, S, or NR$_6$R$_7$;
  each X is independently a halide;

each $R_1$ is independently a bond or $C_1$–$C_4$ alkylene;

each of $R_2$, $R_3$ and $R_4$ is independently H, F, fluorinated $C_1$–$C_{10}$ alkyl, fluorinated $C_4$–$C_{20}$ aryl, $C_3$–$C_{10}$ cycloalkyl, fluorinated $C_3$–$C_{10}$ cycloalkyl, $C_1$–$C_{10}$ alkyl or $C_4$–$C_{20}$ aryl, provided at least one of $R_2$, $R_3$ and $R_4$ is F, fluorinated $C_1$–$C_{10}$ alkyl, fluorinated $C_3$–$C_{10}$ cycloalkyl, or fluorinated $C_4$–$C_{20}$ aryl;

each $R_5$ is independently fluorinated $C_1$–$C_{10}$ alkyl, fluorinated $C_4$–$C_{20}$ aryl, $C_4$–$C_{20}$ aryloxide, fluorinated $C_4$–$C_{20}$ aryloxide, $C_1$–$C_{10}$ alkoxide or fluorinated $C_1$–$C_{10}$ alkoxide;

each of $R_6$ and $R_7$ is independently H or $C_1$–$C_{10}$ alkyl;

each of a, b and c is independently an integer from 0 to 4, provided the sum of a, b and c is an integer from 2 to 8; and n is 1 or 2; and provided that when $R_2$ is a fluorinated $C_1$–$C_4$ alkyl, $R_1$ is a bond, b, and c are 0, and $R_3$ is $C_1$–$C_{10}$ alkyl or fluorinated $C_4$–$C_{10}$ alkyl then $R_4$ is F, fluorinated $C_1$–$C_{10}$ alkyl or fluorinated $C_4$–$C_{20}$ aryl.

Another embodiment of the present invention provides a compound comprising an anion of the formula:

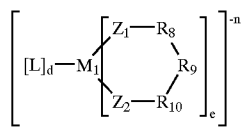

wherein $M_1$ is a transition metal, or a Group III, IV or V element;

L is a halide, $C_1$–$C_{10}$ alkyl, fluorinated $C_1$–$C_{10}$ alkyl, $C_4$–$C_{20}$ aryl, fluorinated $C_1$–$C_{20}$ alkyl or a moiety of the formula –$Z_3$–$R_{11}$;

d is an integer from 0 to 4;

e is an integer from 1 to 3;

the sum of d and e is an integer from 1 to 6;

n is 1 or 2;

each of $Z_1$, $Z_2$ and $Z_3$ is independently O, S, or $NR_6R_7$;

each of $R_6$ and $R_7$ is independently H or $C_1$–$C_{10}$ alkyl;

each $R_9$ is independently $C_1$–$C_{30}$ alkylene, fluorinated $C_1$–$C_{30}$ alkylene, substituted $C_1$–$C_{30}$ alkylene, $C_3$–$C_{10}$ cycloalkylene, fluorinated $C_3$–$C_{10}$ cycloalkylene, $C_4$–$C_{20}$ arylene or fluorinated $C_4$–$C_{20}$ arylene;

each of $R_8$ and $R_{10}$ is a bond, or a moiety of the formula —$[C(R_{12}R_{13})]_x$—;

each x is independently an integer from 1 to 4;

each of $R_{12}$ and $R_{13}$ is independently H, F, $C_1$–$C_4$ alkyl or fluorinated $C_1$–$C_4$ alkyl; and each $R_{11}$ is independently $C_1$–$C_{10}$ alkyl, fluorinated $C_1$–$C_{10}$ alkyl, $C_4$–$C_{20}$ aryl, or fluorinated $C_4$–$C_{20}$ aryl;

provided at least one of $R_8$ and $R_{10}$ is a moiety of the formula —$C(R_{12}R_{13})$— and at least one of $R_{12}$ and $R_{13}$ is F or fluorinated $C_1$–$C_4$ alkyl.

The present invention also provides an electrolyte for an electrochemical device, comprising the anion of the above described formula having a counter cation M where M is a metal cation, a phosphonium cation, an ammonium cation or a sulfonium cation. Preferably M is Li cation.

DETAILED DESCRIPTION OF THE INVENTION

The present invention provides a compound comprising an anion of the formula:

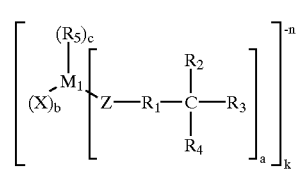

and uses thereof, where $M_1$ is a transition metal, or a Group III, IV or V element, preferably $M_1$ excludes Cu; each Z is independently O, S, or $NR_6R_7$; each X is independently a halide; each $R_1$ is independently a bond or $C_1$–$C_4$ alkylene; each of $R_2$, $R_3$ and $R_4$ is independently H, F, fluorinated $C_1$–$C_{10}$ alkyl, fluorinated $C_4$–$C_{20}$ aryl, $C_3$–$C_{10}$ cycloalkyl, fluorinated $C_3$–$C_{10}$ cycloalkyl, $C_1$–$C_{10}$ alkyl or $C_4$–$C_{20}$ aryl, provided at least one of $R_2$, $R_3$ and $R_4$ is F, fluorinated $C_1$–$C_{10}$ alkyl, fluorinated $C_3$–$C_{10}$ cycloalkyl, or fluorinated $C_4$–$C_{20}$ aryl; each $R_5$ is independently fluorinated $C_1$–$C_{10}$ alkyl, fluorinated $C_4$–$C_{20}$ aryl, $C_4$–$C_{20}$ aryloxide, fluorinated $C_4$–$C_{20}$ aryloxide, $C_1$–$C_{10}$ alkoxide or fluorinated $C_1$–$C_{10}$ alkoxide; each of $R_6$ and $R_7$ is independently H or $C_1$–$C_{10}$ alkyl; each of a, b and c is independently an integer from 0 to 4, provided the sum of a, b and c is an integer from 2 to 8; and n is 1 or 2; provided that when $R_2$ is a fluorinated $C_1$–$C_4$ alkyl, $R_1$ is a bond, b, and c are 0, and $R_3$ is $C_1$–$C_{10}$ alkyl or fluorinated $C_1$–$C_{10}$ alkyl then $R_4$ is F, fluorinated $C_1$–$C_{10}$ alkyl or fluorinated $C_4$–$C_{20}$ aryl.

The present invention also provides a compound comprising an anion of the formula:

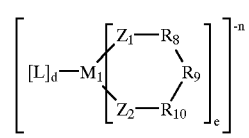

where $M_1$ is a transition metal, or a Group III, IV or V element; L is a halide, $C_1$–$C_{10}$ alkyl, fluorinated $C_1$–$C_{10}$ alkyl, $C_4$–$C_{20}$ aryl, fluorinated $C_4$–$C_{20}$ alkyl or a moiety of the formula —$Z_3$—$R_{11}$; d is an integer from 0 to 4; e is an integer from 1 to 3; the sum of d and e is an integer from 1 to 6; n is 1 or 2; each of $Z_1$, $Z_2$ and $Z_3$ is independently O, S, or $NR_6R_7$; each of $R_6$ and $R_7$ is independently H or $C_1$–$C_{10}$ alkyl; each $R_9$ is independently $C_1$–$C_{30}$ alkylene, fluorinated $C_1$–$C_{30}$ alkylene, substituted $C_1$–$C_{30}$ alkylene, $C_3$–$C_{10}$ cycloalkylene, fluorinated $C_3$–$C_{10}$ cycloalkylene, $C_4$–$C_{20}$ arylene or fluorinated $C_4$–$C_{20}$ arylene; each of $R_8$ and $R_{10}$ is a bond, or a moiety of the formula —$[C(R_{12}R_{13})]_x$—; each x is independently an integer from 1 to 4; each of $R_{12}$ and $R_{13}$ is independently H, F, $C_1$–$C_4$ alkyl or fluorinated $C_1$–$C_4$ alkyl; and each $R_{11}$ is independently $C_1$–$C_{10}$ alkyl, fluorinated $C_1$–$C_{10}$ alkyl, $C_4$–$C_{20}$ aryl, or fluorinated $C_4$–$C_{20}$ aryl; provided at least one of $R_8$ and $R_{10}$ is a moiety of the formula —$C(R_{12}R_{13})$— and at least one of $R_{12}$ and $R_{13}$ is F or fluorinated $C_1$–$C_4$ alkyl.

Preferably, the compound of the present invention has at least two polyfluorinated alkoxide groups bonded to $M_1$. As used herein, a "polyfluorinated anion" refers to an anion of the above described formula.

The polyfluorinated anions of the present invention themselves do not necessarily comprise chemical compounds. Indeed, in an isolable compound, anions must be paired with cations to maintain electroneutrality. Thus, compounds of the present invention are, more accurately, of the formulas:

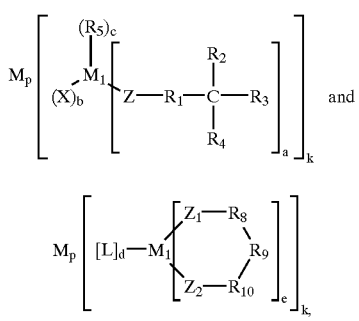

where M is a cation having a valence of from 1 to 4. M can be any cation including a cation derived from an alkali metal; alkaline-earth metal; transition metal such as Ag, Zn, Cu, Co, Fe, Mn, Cr, V, Ti, Zr, Rh, Pd, Cd, Hg, Os, Pt, Y, Nb, Sc, Ta, Hf, and Mo; lanthanide and actinide series metal; ammonium moieties such as ammonium, tetrahydrocarbyl ammonium, e.g., tetrabutyl ammonium and tetraethyl ammonium, trihydrocarbyl ammonium, e.g., triethyl ammonium, diisopropyl ethyl ammonium and trimethyl ammonium, dihydrocarbyl ammonium, nitrogen heteroaromatic cation such as 2,6-lutidinium, methyl 2,6-lutidinium, methyl pyridinium and pyridinium, and imminium cation; phosphonium moieties including tetraalkylphosphonium, tetraaryl phosphonium and phosphonium ions containing a mixture of alkyl and aryl groups; sulfonium moieties such as sulfonium ions containing alkyl, aryl or mixtures thereof; and other suitable cations such as thallium. Furthermore, M can be a relatively stable carbocation such as a trityl moiety and related carbocations (e.g., $R_3C^+$); and other known cations such as hydronium ($H_3O^+$), $H_5O_2^+$, $(Et_2O)_nH^+$, $H_9O_4^+$, and formylium ($HCO^+$). Preferably, the cation (i.e., M) is selected from the group consisting of thallium, alkali metal and alkaline earth metal cations, ammonium, monohydrocarbyl ammonium, dihydrocarbyl ammonium, trihydrocarbyl ammonium, tetrahydrocarbyl ammonium, nitrogen heteroaromatic cation, tetrahydrocarbyl phosphonium, hydronium, formylium, and trityl and related carbocations; more preferably from the group consisting of trityl and related carbocations, thallium, tetrahydrocarbyl ammonium, alkali metal cations, and nitrogen heteroaromatic cation; and most preferably from the group consisting of trityl, $Li^+$, $Tl^+$, 2,6-lutidinium, tetraethylammonium, sodium, potassium, and N-methyl-2,6-lutidinium. As used in this invention, a "hydrocarbyl" refers to a compound having at least one carbon atom. Such compounds include aryl, alkyl, alkenyl and alkynyl. Moreover, hydrocarbyl can be straight chain, branched, or cyclic. Hydrocarbyl can also be substituted with other non hydrogen or carbon atoms such as halide, oxygen, sulfur, nitrogen or phosphorus.

It will be appreciated that a molar ratio of a cation to a polyfluorinated anion of the present invention depends on the valence of the cation. This is reflected in the values p and k, for example, if both the cation and the anion are monovalent, then k and p are 1, and there will be a 1:1 molar ratio between the cation and the polyfluorinated anion of the present invention. Whereas if the cation is divalent and the anion is monovalent, then k is 2 and p is 1, and there will be a 1:2 molar ratio between the cation and the polyfluorinated anion of the present invention. Preferably, k is an integer from 1 to 4, more preferably 1 to 3, still more preferably k is 1 or 2, and most preferably 1. Preferably p is 1 or 2 and more preferably 1.

It should be appreciated that because the polyfluorinated anions of the present invention are weakly associating (i.e., coordinating) anions, a cation associated with a polyfluorinated anion can be readily exchanged with another cation by any of the known methods including ion exchange chromatography and other ion exchange methods.

As used in this invention, Group III, IV and V elements are those elements which are listed in the Group III, IV and V of the periodic table, respectively. For example, Group III elements are B, Al, Ga, In and Tl; Group IV elements are C, Si, Ge, Sn, and Pb; and Group V elements are N, P, As, Sb and Bi.

With reference to formulas I–IV described herein:

Preferably $M_1$ is selected from the group consisting of Al, B, V, Ti, Si, Zr, Ge, Sn, Cu, Y, Zn, Ga, Nb, Ta, Bi, P, As, Sc, Hf and Sb, more preferably from the group consisting of Al, B, V, Ti, Si, Zr, Ge, Sn, Y, Zn, Ga, Nb, Ta, Bi, P, As, Sc, Hf and Sb, still more preferably from the group consisting of Al, B, Nb and Ta, and most preferably from the group consisting of Al and B.

Preferably, Z, $Z_1$, $Z_2$ and $Z_3$ are O.

Preferably n is 1.

Preferably a is 1, 3 or 4, more preferably 4.

Preferably b is 0 or 1.

Preferably c is 0 or 3.

Preferably the sum of a, b and c is an integer from 2 to 8, more preferably an integer from 4 to 8, still more preferably an integer from 4 to 6, and most preferably 4.

Preferably X is fluoride.

Preferably $R_5$ is fluorinated $C_4$–$C_{20}$ aryl or fluorinated $C_4$–$C_{20}$ aryloxide, more preferably fluorinated phenyl or phenoxide, and most preferably 2-trifluoromethylphenoxide, 3-trifluoromethylphenoxide, 4-trifluoromethylphenoxide, pentafluorophenoxide, or pentafluorophenyl.

Preferably $R_1$ is a bond or methylene.

Preferably each of $R_2$, $R_3$ and $R_4$ is independently H, F, fluorinated $C_1$–$C_4$ alkyl, $C_4$–$C_{20}$ aryl or fluorinated $C_4$–$C_{20}$ aryl. More preferably each of $R_2$, $R_3$ and $R_4$ is independently H, F, trifluoromethyl, phenyl, 4-methylphenyl, methyl, n-butyl, 4-tert-butylphenyl, 3,5,-di(trifluoromethyl)phenyl, 3,5,-dimethylphenyl, 2,4,6-tri(trifluoromethyl)phenyl, 4-(triisopropylsilyl)-2,6-di(trifluoromethyl)phenyl, tert-butyl, cyclohexyl or pentafluorophenyl.

Preferably L is a halide or a moiety of the formula —$Z_3$—$R_{11}$, $C_1$–$C_{10}$ alkyl, fluorinated $C_1$–$C_{10}$ alkyl, $C_4$–$C_{20}$ aryl or fluorinated $C_4$–$C_{20}$ alkyl; more preferably L is F, pentafluorophenyl, or a moiety of the formula —$Z_3$—$R_{11}$.

Preferably d is an integer from 0 to 6, more preferably an integer from 0 to 4, and most preferably d is 0 or 2.

Preferably e is an integer from 1 to 4, more preferably an integer from 1 to 2 and most preferably e is 2.

Preferably, the sum of d and e is an integer from 1 to 6, more preferably 2 to 4.

Preferably $R_{11}$ is fluorinated $C_1$–$C_{10}$ alkyl.

Preferably $R_9$ is substituted or unsubstituted $P_1,P_2$-substituted arylene or fluorinated arylene, or substituted or unsubstituted $P_1,P_2$-substituted cycloalkylene or fluorinated cycloalkylene, such as cyclopentylene, and preferably cyclohexylene. As used in this invention, $P_1,P_2$-substituted arylene/cycloalkylene refers to an arylene/cycloalkylene moiety in which —$Z_1$—$R_8$— and —$Z_2$—$R_{10}$— groups are in $P_1$- and $P_2$-positions of the arylene/cycloalkylene moiety, respectively. Thus, for example, 1,2-substituted phenylene refers to a phenylene group having —$Z_1$—$R_8$— in the 1-position of the phenyl ring and —$Z_2$—$R_{10}$— group in the 2-position of the phenyl ring. "Substituted or unsubstituted" refers to the presence or absence of one or more substituents on the phenyl (or other appropriate) ring moiety, respectively. Such substituents can be F, Cl; Br; I; an alkyl group including cyclic alkyl and alkyl groups containing F, Cl, Br and/or I; and an aryl group including aryl groups containing F, Cl, Br and/or I and heteroaryl groups. For an electrolyte, $R_9$ can also be $C_1$–$C_4$ alkylene or fluorinated $C_1$–$C_4$ alkylene, in particular —$C(CF_3)_2$— moiety.

Preferably x is a bond or 1.

Preferably each of $R_{12}$ and $R_{13}$ are independently fluorinated $C_1$–$C_4$ alkyl. More preferably $R_{12}$ and $R_{13}$ are independently trifluoromethyl or perfluoroethyl, most preferably $R_{12}$ and $R_{13}$ are trifluoromethyl.

Alkyl groups according to the present invention are aliphatic hydrocarbons which can be straight or branched chain groups. Alkyl groups optionally can be substituted with one or more substituents, such as Cl, Br, I, alkenyl, alkynyl, aryl, hydroxy, alkoxy, carboxy, oxo or cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, chloromethyl, trichloromethyl, and pentafluoroethyl. Alkyl groups containing at least one fluorine is specifically refered herein as fluorinated alkyl groups.

Aryl groups are carbocyclic or heterocyclic aromatic ring moieties. Aryl groups can be substituted with one or more substituents, such as a Cl, Br, I, alkenyl, alkyl, alkynyl, hydroxy, alkoxy or cycloalkyl. Exemplary aryl groups include, phenyl, p-methylphenyl, p-tert-butylphenyl, thienyl, furanyl, pyrimidinyl, pyridyl, oxazolyl, isoxazolyl, and thiophenyl. Aryl groups containing at least one fluorine is specifically refered herein as fluorinated aryl groups.

$M_1$ of the polyfluorinated anion of the present invention may contain a mixture of polyfluorinated alkoxide and non-fluorinated alkoxide ligands.

Specific polyfluoroalkoxide ligands for anion of formula I (i.e., compound of formula III), include, but are not limited to, the following ligands:

a polyfluoroalkoxide ligand where Z is O, $R_1$ is methylene, b and c are 0, a is 4, and $R_2$, $R_3$ and $R_4$ are F; and polyfluoroalkoxides where Z is O and $R_1$ is a bond, and
$R_2$ is trifluoromethyl, and each of $R_3$ and $R_4$ is independently phenyl or methyl;
$R_2$, $R_3$ and $R_4$ are trifluoromethyl;
$R_2$ is trifluoromethyl, $R_3$ is phenyl, and $R_4$ is phenyl or pentafluorophenyl; and
$R_2$ and $R_3$ are phenyl, and $R_4$ is pentafluorophenyl.

Specific polyfluoroalkoxide ligands for anion of formula II (i.e., compound of formula IV), include, but are not limited to, the following ligands:

n is 1 and the —$Z_1$—$R_8$—$R_9$—$R_{10}$—$Z_2$— moiety comprises:

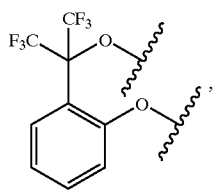
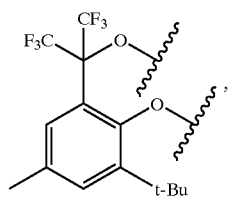

-continued

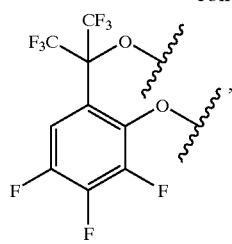
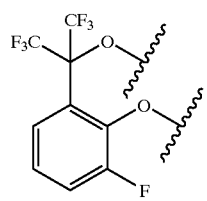

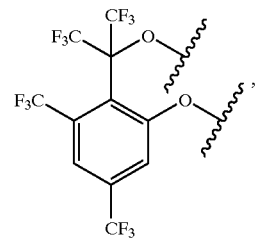
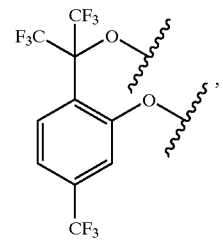

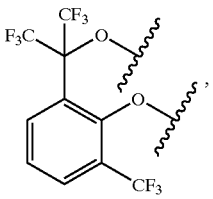
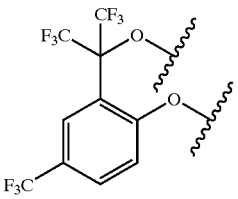

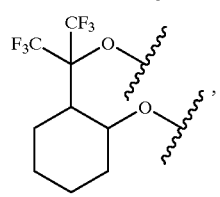

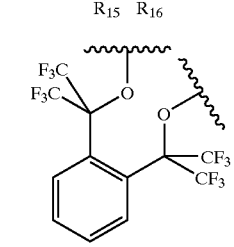

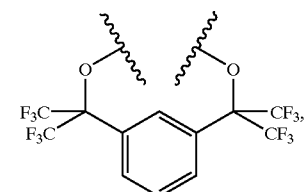

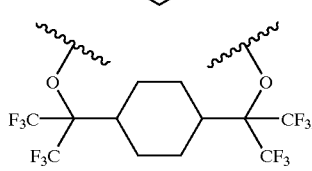

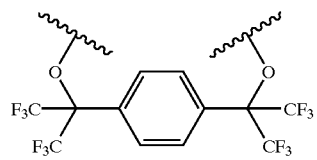

-continued

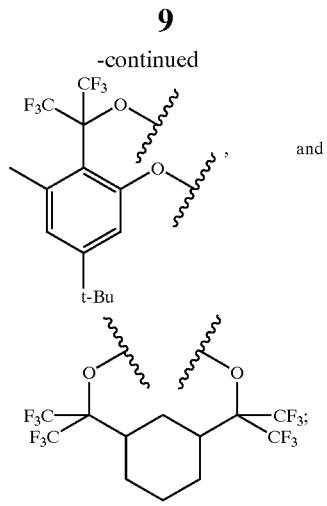

where each of $R_{14}$, $R_{15}$, $R_{16}$, and $R_{17}$ is independently H, $C_1-C_{10}$ alkyl, fluorinated $C_1-C_{10}$ alkyl, $C_4-C_{20}$ aryl, or fluorinated $C_4-C_{20}$ aryl. Preferably, $R_{14}$ and $R_{17}$ are trifluoromethyl, $R_{15}$ is H, and $R_{16}$ is phenyl.

Unlike other anions containing chelating dialkoxide groups, compounds II and IV of the present invention have improved stability (thermal, hydrolytic and electrochemical) lower toxicity, and/or higher synthetic yields. Moreover, compounds of the present invention, in particular lithium salts, have high conductivity making them particularly useful as electrolytes in electrochemical devices.

A variety of counter-cation species, including metal cations such as Li, K, Na, Mg, Ca, and Cs; trityl cation; pyridinium cations such as 2,6-pyridinium cation; and 2,6-lutidinium cation, can be prepared from the anions of the present invention. For example, by cation-exchange reaction, the trityl ($CPh_3^+$) salt can be prepared by metathesis of Li salt of the anions with $CPh_3Cl$ in 1,2-dichloroethane.

Without being bound by any theory, it is believed that the high conductivity of lithium salts of the compounds of the present invention is due to $Li^+$ ion being weakly bonded to several alkoxide oxygen atoms and possibly being bonded to several $CF_3$-group fluorine atoms, similar to $Tl^+$ ions in $Tl_2Zr(HFIP)_6$. In contrast, the $Li^+$ ion in the unfluorinated salt $LiNb(OEt)_6$ is believed to be strongly bonded to only four ethoxide oxygen atoms from two adjacent $Nb(OEt)_6^-$ anions forming a pseudo-tetrahedral $LiO_4$ core.

Compounds containing the polyfluorinated anion of the present invention have high electrical conductivity making them particularly useful as electrolytes for electrochemical devices. Exemplary electrochemical devices include batteries, such as lithium batteries or lithium ion batteries for a variety of applications; other type of batteries; fuel cells; electrical double layer capacitors; sensors; and electrochromic displays. Such electrochemical devices can be used in a variety of applications including electrochemical devices for electric vehicles, lap top computers, and other applications requiring an energy source. As table 1 shows, lithium salts of the polyfluorinated anions of the present invention have high electrical conductivities in organic solvents. Specifically, the compounds of the present invention have high electrical conductivity in DME compared to other fluorine-containing lithium salts such as LiOTf.

TABLE 1

Electrical Conductivity[1]

| Compound | Conc. (M) | Solvent | Conductivity (mS cm$^{-1}$) | Eq. conductivity (S cm$^2$ mol$^{-1}$) |
|---|---|---|---|---|
| Li(HFIP) | 0.0100 | DME | ~0 | |
| LiOTf | 0.0100 | DME | 0.00390 | 0.390 |
| LiOTf/1.36 eq. crown | 0.0100 | DME | 0.00700 | 0.700 |
| LiOTf/>50 eq. crown | 0.0100 | DME | 0.0310 | 3.10 |
| LiOTf | 0.0100 | PC | 0.195 | 19.5 |
| LiB ($C_6F_5$)$_3$ (HFIP) | 0.0100 | DME | 0.176 | 17.6 |
| LiB ($C_6F_5$)$_3$ (DPTE) | 0.0100 | DME | 0.129 | 12.9 |
| LiB ($C_6F_5$)$_3$ (PFTB) | 0.0100 | DME | 0.137 | 13.7 |
| LiB (HFPOP)$_2$ | 0.0100 | DME | 0.137 | 13.7 |
| LiB (HFPOP)$_2$ | 0.100 | DME | 1.58 | 15.8 |
| LiB (HFPOP)$_2$ | 0.200 | DME | 3.05 | 15.2 |
| LiB (HFPOP)$_2$ | 0.300 | DME | 4.49 | 15.0 |
| LiB (HFPOP)$_2$ | 0.400 | DME | 5.30 | 13.2 |
| LiB (HFPOP)$_2$ | 0.500 | DME | 5.88 | 11.8 |
| LiB (HFPOP)$_2$ | 0.600 | DME | 5.83 | 9.7 |
| LiB (HFPOP)$_2$ | 0.0100 | PC | 0.133 | 13.3 |
| LiB (HFAPOP)$_2$ | 0.0100 | DME | 0.160 | 16.0 |
| LiB (HFAPOP)$_2$ | 0.100 | DME | 1.77 | 17.7 |
| LiB (HFAPOP)$_2$ | 0.300 | DME | 4.22 | 14.1 |
| LiB (HFAPOP)$_2$ | 0.500 | DME | 4.35 | 8.69 |
| LiB (HFTPOP)$_2$ | 0.0100 | DME | 0.218 | 21.8 |
| LiB (HFTPOP)$_2$ | 0.500 | DME | 8.23 | 16.5 |
| LiAl (HFIP)$_4$ | 0.0100 | DME | 0.183 | 18.3 |
| LiAl (TFTB)$_4$ | 0.0100 | DME | 0.0693 | 6.93 |
| LiAl (DPTE)$_4$ | 0.0100 | DME | 0.205 | 20.5 |

[1]HFIP$^-$ = OCH(CF$_3$)$_2^-$; DPTE$^-$ = OC(CF$_3$)(C$_6$H$_5$)$_2^-$; TFTB$^-$ = OC(CF$_3$)(CH$_3$)$_2^-$; PFTB$^-$ = OC(CF$_3$)$_3^-$; HFPOP$^{-2}$ = OC(CF$_3$)$_2$(C$_6$H$_4$O)$^{-2}$; HFAPOP$^{-2}$ = OC(CF$_3$)$_2$[C$_6$H$_2$(CH$_3$)(C$_4$H$_9$)O]$^{-2}$; HFTPOP$^{-2}$ = OC(CF$_3$)$_2$(C$_6$HF$_3$O)$^{-2}$; OTf$^-$ = CF$_3$SO$_3^-$; crown = 12-crown-4; PC = propylene carbonate; DME = 1,2-dimethoxyethane.

Particularly useful lithium salts of the compounds of the present invention in batteries include LiB(HFPOP)$_2$, LiB (HFAPOP)$_2$, and LiB (HFTPOP)$_2$.

Again referring to Table 1, the lithium salts of the polyfluorinated anions of the present invention are at least about two orders of magnitude higher in electrical conductivity than lithium triflate. Thus, the amount of a compound of the present invention required in an electrochemical device to achieve a similar electrical conductivity in an organic solvent such DME is about 1% of the amount of other fluorine-containing electrolytes such as LiCF$_3$SO$_3$.

A lithium salt of the polyfluorinated anion of the present invention has an electrical conductivity of at least about 4 $\mu$Scm$^{-1}$ in DME at about 0.01 M concentration at about 25° C., preferably at least about 60 $\mu$Scm$^{-1}$, more preferably at least about 150 $\mu$Scm$^{-1}$, and most preferably at least about 180 $\mu$Scm$^{-1}$.

Without being bound by any theory, it is believed that the weak bonds between the Li$^-$ cation and the CF$_3$ groups are responsible for the high electrical conductivity in low dielectric solvents. Indeed, it is believed that the high degree or fluorination and the weak coordination between the Li$^+$ cations in the C-F bonds differentiate the lithium salts of the present invention from other fluorine-containing lithium salts.

The electrochemical stability of a representative compound is shown in Table 2 below. Specifically, Table 2 lists anodic stability of a compound containing a chelating group HFTPOP, e.g., a bidentate group. The anodic stability shows the relative stability of the compound and the potential for oxidation of an anode containing the compound relative to lithium.

TABLE 2

Anodic Stability

| Compound | Solvent | Conc. (M) | Potential vs. Li/Li$^+$ (V) |
|---|---|---|---|
| LiB (HFTPOP)$_2$ | DME | 0.1 | 4.7 |
| LiAl (HFPP)$_4$ | DME | 0.07 | >5.2 |

Conditions: Sweep rate: 5 mV/s; T = 25° C.; Reference electrode: Li wire; Working electrode Pt; Counter electrode: Pt mesh.

The polyfluorinated anions of the present invention can also be used in a variety of organic reaction catalysts where a weakly coordinating anion improves the yield, selectivity and/or the rate of catalytic reaction by the corresponding cation including in catalysts for conjugate additions and Diels-Alder reactions. The compounds of the present invention comprise a weakly coordinating anion, i.e., polyfluorinated anion, which enhances the catalytic activity of the associated metal cation. Exemplary catalytic reactions that have recently received a considerable attention are lithium-catalyzed Diels-Alder reactions and lithium-catalyzed 1,4-conjugate addition reactions. As shown below, using LiNb (HFIP)$_6$, 1, as a catalyst in 1,4-conjugate addition reaction of silyl ketene acetal 2 to the sterically encumbered α,β-unsaturated carbonyl compound 3 gave the 1,4-addition product 4 in 93% yield.

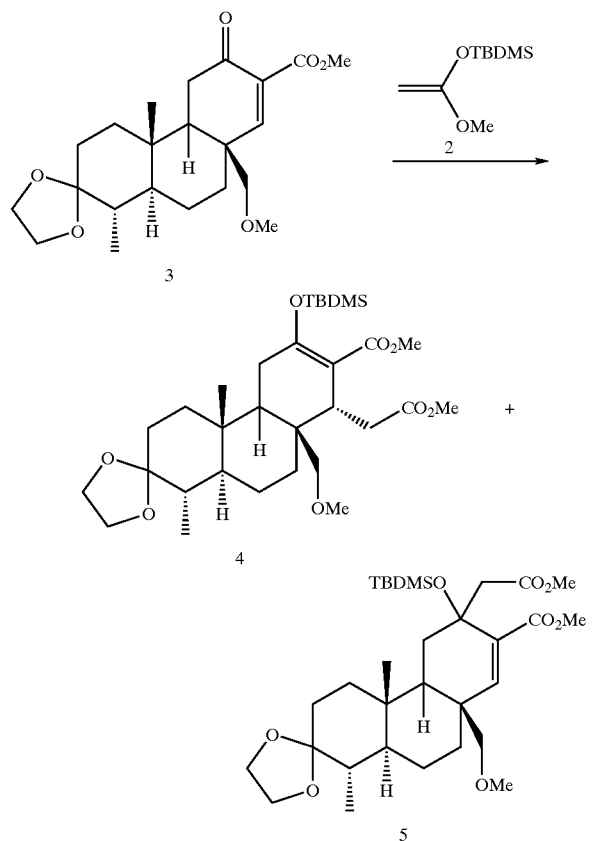

Reaction conditions: 1,2-dichloroethane (DCE) solvent, 0.1 M of 3, 0.2 M of 2, 0.01 M of LiNb(HFIP)$_6$ and 0.01 M of hexamethylphosphoramide (HMPA) at 24° C. for 30 hours.

Formation of only the 1,4-addition product 4 was observed under these conditions. Interestingly, when HMPA was left out of the reaction mixture, a mixture of 4 and the 1,2-addition product 5 was observed after only 10 minutes (95% isolated yield, 4:5 mole ratio=1:5). Without being bound by any theory, it is believed that Li$^+$ ion coordinates with HMPA to produce a sterically more hindered enone-lithium ion complex, thus favoring addition of the ketene at a site more distant from the carbonyl carbon, i.e., 1,4-addition, over addition of the ketene to the carbonyl carbon, i.e., 1,2-addition reaction. Because lithium compounds of the present invention are similar to lithium compounds disclosed in PCT Patent Application No. PCT/US98/19268 and U.S. patent application Ser. No. 09/151,852, lithium compounds of the present invention are expected to provide a similar reaction selectivity.

A comparison of the ability of LiNb(HFIP)$_6$ and two other lithium catalysts to increase the formation of 1,4-conjugate addition product is shown in Table 3. The weaker Lewis acidity of the Li(HMPA)$^+$ complex results in a decreased reaction rate, which is evidenced by the longer reaction time required when HMPA is added to the reaction mixture. The results obtained with LiNb(HFIP)$_6$ are comparable to the results obtained with the very active catalyst LiCo(C$_2$B$_9$H$_{11}$)$_2$. Product yields were substantially lower when LiClO$_4$ was the catalyst. Furthermore, when LiClO$_4$ was employed in the presence of co-catalyst HMPA, the ratio of 4:5 improved only to 1.3:1. Without being bound by any theory, it is believed that the larger size and/or more weakly coordinating ability of Nb(HFIP)$_6^-$ to Li$^+$ compared with ClO$_4^-$ is responsible for the difference in catalytic activity between LiClO$_4$ and LiNb(HFIP)$_6$.

TABLE 3

Yields of 1, 4- and 1, 2-addition products 4 and 5, respectively, from lithium-catalyzed reactions between 2 and 3[a]

| catalyst | co-catalyst[b] | time | 4:5 ratio | % yield |
|---|---|---|---|---|
| LiNb (HFIP)$_6$ | none | 10 min | 1:5 | 95% |
| LiNb (HFIP)$_6$ | 0.1 M HMPA | 30 h | 100:0 | 93% |
| LiCo (C$_2$B$_9$H$_{11}$)$_2$[c] | none | 20 min | 1:6 | 95% |
| LiCo (C$_2$B$_9$H$_{11}$)$_2$[c] | 0.1 M HMPA | 32 h | 100:0 | 96% |
| LiClO$_4$ | none | 10 min | 1:4.5 | 62% |
| LiClO$_4$ | 0.1 M HMPA | 48 h | 1.3:1 | 69% |

[a]Reaction conditions: 1,2-dichloroethane, 0.1 M of 3, 0.2 M of 2, 0.1 M of catalyst and 0.1 M of co-catalyst, when appropriate, at 25° C.).
[b]HMPA = hexamethylphosphoramide.
[c]These results are from DuBay et al., J. Org. Chem., 1994, 59, 6898.

The polyfluorinated anions of the present invention that are sterically bulkier, i.e., larger, than Nb(HFIP)$_6^-$ afford lithium-ion catalysts that are more regioselective and/or more active in the absence of HMPA. Moreover, enantiomerically enriched polyfluorinated anions of the present invention containing a polyfluorinated alkoxide having a chiral center afford lithium-ion catalysts that are enantioselective, i.e., produce an enantiomerically enriched product. A chiral center of a carbon atom, of course, is a carbon atom to which four different groups are attached; however, the ultimate criterion of chirality of a compound is nonsuperimposability on the mirror image. Facially selective, enantioselective or stereoselective synthetic reactions are those in which one of a set of stereoisomers is formed predominantly or exclusively. Preferably, one isomer is produced in at least about 50 percent enantiomeric excess. Enantiomeric excess is the amount of difference between one enantiomer and the other enantiomer in the product composition. Enantiomeric excess can be expressed by the following formula: %ee=(R−S)/(R+S), where R is amount of one enantiomer and S is the amount of the other enantiomer, for example, %ee of a product composition containing 98% of one enantiomer and 2% of the other enantiomer is 96%. More preferably, one isomer is produced in at least about 80 percent enantiomeric excess, still more preferably at least about 90 percent enantiomeric excess, even more preferably at least about 95 percent enantiomeric excess, and most preferably at least about 98 percent excess over the other enantiomer.

Lithium salts of the polyfluorinated anions of the present invention can be combined or mixed with a polymer to prepare polymeric materials that exhibit lithium ion conductivity. Such materials, referred to as salt-in-polymer solid electrolytes or solid polymer electrolytes, can be used as electrolytes for solvent-free high-energy-density lithium-based batteries. A polymer can also include a linker which allows a direct linkage of the compound of the present invention to the polymeric structure by a chemical bond formation between the polymer and the compound of the present invention. The polymers useful for the present invention have a rubbery physical characteristic. Generally, suitable polymers have one or more of the following identifying characteristics: 1) ability to dissolve lithium salts of weakly coordinating anions and/or to coordinate, albeit weakly, to the lithium cations of lithium salts of weakly coordinating anions; 2) ability to maintain low glass-transition temperatures with varying amounts of lithium salts dissolved therein; and 3) the ability to possess high electrical conductivities, especially high lithium-ion conductivities, i.e., higher than lithium triflate/polymer mixture at a given temperature). Exemplary polymers useful for the present invention include polyethylene glycol; polyethylene; polypropylene; polystyrene; polybutadiene; poly (vinyl fluoride); polychloroprene; poly(alkyl siloxane) such as poly(dimethylsiloxane); poly(vinyl chloride); poly (ethylene imine); and poly(alkylene oxide) such as poly (propylene oxide), amorphous poly(ethylene oxide) and poly(ethylene oxide). Preferably the polymer is selected from the group consisting of amorphous polyethylene oxide (aPEO), poly(alkylene oxide), poly(alkyl siloxane), poly (vinyl fluoride), poly(vinyl chloride), polychloroprene, polybutadiene, polyethylene and poly propylene; more preferably from the group consisting of aPEO, poly(vinyl fluoride), poly(vinyl chloride), polychloroprene, polybutadiene, polyethylene and polypropylene; and most preferably from the group consisting of aPEO, polybutadiene, polyethylene and polypropylene.

The present invention also includes salt-in-polymer electrolytes having alkali metal salts containing the polyfluorinated anions of the present invention. Compounds containing these polyfluorinated anions have superior glass transition temperatures, impedance measurements and cation transference numbers than compounds containing other anions.

The polyfluorinated anions of the present invention can also be used as co-catalysts for activating transition-metal-catalyzed olefin polymerization and as counterions for polymerization photoinitiators.

Additional objects, advantages, and novel features of this invention will become apparent to those skilled in the art upon examination of the following examples thereof, which are not intended to be limiting.

EXAMPLES

Example 1
Synthesis of $LiB(C_6F_5)_3(HFIP)$ $B(C_6F_5)$ (0.0256 g, 0.05 mmol) and LiHFIP (0.0087 g, 0.05 mmol) were dissolved in 5 mL of DME to make a clear, colorless solution.

Example 2
Synthesis of $LiB(C_6F_5)(DPTE)$ $B(C_6F_5)$ (0.0256 g, 0.05 mmol) and LiDPTE (0.0129 g, 0.05 mmol) were dissolved in 5 mL of DME to make a clear, colorless solution.

Example 3
Synthesis of $LiB(C_6F_5)_3(PFTB)$ $B(C_6F_5)$ (0.0256 g, 0.05 mmol) and LiPFTB (0.0121 g, 0.05 mmol) were dissolved in 5 mL of DME to make a clear, colorless solution.

Example 4
Synthesis of $LiAl(DPTE)_4$

Hexane (40 mL) was added to $LiAlH_4$ (0.0188 g, 0.4955 mmol) to make a suspension. To this was added H(DPTE) (0.500 g, 1.982 mmol) as a hexane solution (10 mL). The reaction mixture was stirred for 4 day at room temperature under an argon atmosphere, after which time a considerable amount of a white solid material was present in a clear and colorless solution. The mixture was filtered through a medium frit. The white solid was washed with hexane, then dissolved in toluene. Toluene was removed under vacuum to leave a white solid that was heated at 105° C. for 18 h. A $^1H$ NMR spectrum of this white solid revealed that approximately 3 mol-% of the alcohol H(DPTE) still remained, but the compound $LiAl(DPTE)_4$ was otherwise pure.

$^1H$ NMR $(C_6D_6/C_6F_6)$ δ7.26 (d, 16 H), 7.00 (m, 24 H). $^{19}F$ NMR$(C_6D_6/C_6F_6)$ δ–72.40 (s). Low Resolution mass spectrum (negative ion electrospray, $CH_3CN$ solution): m/z 1031 (M-Li)$^-$; calc'd for $C_{56}H_{40}AlF_{12}O_4$ 1031.6.

Example 5
Synthesis of $Li(DME)_2Al(TFTB)_4$

Hexane (30 mL) was added to $LiAlH_4$ (0.0976 g, 2.57 mmol) to make a suspension. To this was added H(TFTB) (1.3155 g, 10.28 mmol) as a hexane solution (20 mL). The reaction mixture was stirred for 3 day at room temperature then at reflux for 3 days under an argon atmosphere. After this time almost no solid was present in solution. The mixture was filtered through a medium frit, to leave an off-white solid and a slightly tan, clear solution. Hexane was removed from the latter under vacuum to leave a white solid. This was sublimed at 90° C. under vacuum to yield a white powder. The solid was dissolved in DME and stirred for 2 h, after which time solvent was removed to yield a white powder.

$^1H$ NMR $(C_6D_6/C_6F_6)$ δ2.89 (DME, s, 6 H), 2.68 (DME, s, 4 H), 1.53 (s, 12 H). $^{19}F$ NMR$(C_6D_6/C_6F_6)$ δ–84.62 (s).

Example 6
Synthesis of $LiAl(HFIP)_4$

Freon-113 (40 mL) was added to $LiAlH_4$ (0.1630 g, 4.29 mmol) to make a suspension. This was cooled to 0° C. in an ice bath, and H(HFIP) (2.8826 g, 17.16 mmol) was added dropwise as a solution in 10 mL Freon-113. This mixture was stirred at 0° C. for 24 h, then at room temperature for 4 days. After this time, the solution was white and cloudy. Freon-113 was removed under vacuum to leave a white solid, which was found to be 97.4% pure by $^{19}F$ NMR.

$^1H$ NMR $(CD_3CN/C_6F_6)$ δ4.6 (m, 4 H). $^{19}F$ NMR $(CD_3CN/C_6F_6)$ δ–76.15 (d). Low Resolution mass spectrum (negative ion electrospray, $CH_3CN$ solution): m/z 694.9 (M-Li)$^-$; calc'd for $C_{12}H_4AlF_{24}O_4$ 695.1.

Example 7
Synthesis of $LiB(HFPOP)_2$ $H_2(HFPOP)$ (2.0029 g, 7.7 mmol), $LiOH.H_2O$ (0.1541 g, 3.67 mmol), and $B(OH)_3$ (0.2267, 3.67 mmol) were dissolved in 115 mL distilled water. Under an argon atmosphere, the mixture was stirred at 105° C. for 18 h. After this time, the solution was clear and colorless. It was opened to air, and water was removed using a rotary evaporator to leave a clear, colorless oil. This was first dried by azeotropic distillation with toluene to leave a white powder, followed by heating at 197° C. under vacuum ($10^{-3}$ torr) for a period of 18 h. Yield: 1.7856 g (91%) isolated as a white solid.

$^1$H NMR (CD$_3$CN/C$_6$F$_6$) δ7.37 (d, 2 H), 7.24 (t, 2 H), 6.79 (t, 2H), 6.7 (d, 2 H). $^{19}$F NMR(CD$_3$CN/C$_6$F$_6$) δ –75.00 (s). Low Resolution mass spectrum (negative ion electrospray, CH$_3$CN solution): m/z 527.1 (M-Li)$^-$; calc'd for C$_{18}$H$_8$BF$_{12}$O$_4$ 527.0.

Example 8
Synthesis of LiB(HFAPOP)$_2$

LiOH.H$_2$O (0.1522 g, 3.62 mmol) and B(OH)$_3$ (0.2241 g, 3.62 mmol) were dissolved in 115 mL distilled water and heated at reflux for 18 h. H$_2$(HFAPOP) (2.5120 g, 7.61 mmol) was then added as a solid along with diethyl ether (15 mL). This mixture was heated to 100° C. and stirred for 18 h. After this time, the reaction mixture was a clear and colorless solution. Diethyl ether and water were removed using a rotary evaporator to leave a clear, colorless oil. This was first dried by azeotropic distillation with toluene to leave an off-white powder, followed by heating at 104° C. under high-vacuum conditions ($10^{-5}$ torr) for 7 days. Yield: 1.9749 g (82%) isolated as an off-white solid.

$^1$H NMR (C$_6$D$_6$/C$_6$F$_6$) δ7.37 (m, 2 H), 7.133 (s, 1 H), 7.127 (s, 1 H), 2.07 (s, 6 H), 1.27 (s, 18 H). $^{19}$F NMR(C$_6$D$_6$/C$_6$F$_6$) δ –72.81 (m), –76.44 (m). Low Resolution mass spectrum (negative ion electrospray, CH$_3$CN solution): m/z 667.3 (M-Li)$^-$; calc'd for C$_{28}$H$_{28}$BF$_{12}$O$_4$ 667.1.

Example 9
Synthesis of LiB(HFTPOP)$_2$

LiOH.H$_2$O (0.156 g, 3.72 mmol) and B(OH)$_3$ (0.230 g, 3.72 mmol) were dissolved in 50 mL distilled water and heated at reflux for 1 h. The compound H$_2$(HFTPOP) (2.45 g, 7.44 mmol) was then added as a solid along with diethyl ether (10 mL). This mixture was heated to 100° C. and stirred for 18 h. After this time, the reaction mixture was a clear and colorless solution. Diethyl ether and water were removed using a rotary evaporator to leave a clear, colorless oil. This was first dried by azeotropic distillation with toluene, followed by heating at 190° C. under high-vacuum conditions ($10^{-3}$ torr) for 18 h. Yield: 2.08 g (87%).

$^1$H NMR (CD$_3$CN/C$_6$F$_6$) δ7.12 (m, 2 H). $^{19}$F NMR (CD$_3$CN/C$_6$F$_6$) δ –75.42 (s), –148.75 (m), –157.38 (m). Low Resolution mass spectrum (negative ion electrospray, CH$_3$CN solution): m/z 634.8 (M-Li)$^-$; calc'd for C$_{18}$H$_2$BF$_{18}$O$_4$ 635.0.

Example 10

This example illustrates a method for preparing salt-in-polymer electrolytes containing the polyfluorinated anion of the present invention.

Samples of aPEO containing different stoichiometric amounts of LiNb(HFIP)$_6$ were prepared as follows. A sample of the polymer (typically 0.13 g, 3.0 mmol ether-oxygen atoms) was mixed with tetrahydrofuran (7 mL). The resulting mixture was mixed with a tetrahydrofuran solution containing varying amounts of LiNb(HFIP)$_6$ so that the ether-oxygen/lithium molar ratio was 12, 24, or 30. The reaction mixture was stirred for 15 hours, after which time a colorless homogeneous solution was observed. Volatiles were removed from the reaction mixture by vacuum evaporation, resulting in a clear, colorless, rubbery solid on the walls of the flask. The rubbery solid was heated under vacuum at 60° C. for 12 hours to ensure complete removal of tetrahydrofuran. The three clear, colorless, rubbery, salt-in-polymer electrolytes prepared in this way were aPEO$_{12}$LiNb(HFIP)$_6$, aPEO$_{24}$LiNb(HFIP)$_6$, and aPEO$_{30}$LiNb(HFIP)$_6$.

Example 11
Synthesis of LiAl[O(C$_6$H$_4$)C(CF$_3$)$_2$O]$_2$

About 0.515 g of HO(C$_6$H$_4$)C(CF$_3$)$_2$OH (1.98 mmol) and 0.155 g of LiAlH$_4$ (4.09 mmol) were mixed in toluene and stirred for 140 h. The reaction mixture was filtered through a Schlenk filter with Celite. The filtrate was concentrated under vacuum to leave a brown solid.

$^1$H NMR (C$_6$D$_6$) δ7.76 (doublet, 1 H), 7.37 (doublet, 1 H), 6.93 (triplet, 1 H), 6.73 (triplet, 1 H), 6.65 (triplet, 1 H), 6.56 (triplet, 1 H), 6.45 (doublet, 1 H), 6.03 (doublet, 1 H). $^{19}$F NMR (C$_6$D6) δ –72.47 (multiplet), –74.06 (multiplet), –78.15 (multiplet), –78.75 (multiplet).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:
1. A compound comprising a monoanion of the formula:

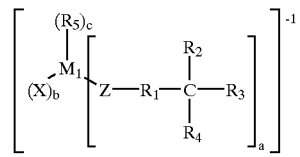

wherein
M$_1$ is a transition metal, or a Group III, IV or V element provided M$_1$ is not Cu;
each Z is independently O, S, or NR$_6$R$_7$;
each X is independently a halide;
each R$_1$ is independently a bond or C$_1$–C$_4$ alkylene;
each of R$_2$, R$_3$ and R$_4$ is independently H, F, fluorinated C$_1$–C$_{10}$ alkyl, fluorinated C$_4$–C$_{20}$ aryl, C$_3$–C$_{10}$ cycloalkyl, fluorinated C$_3$–C$_{10}$ cycloalkyl, C$_1$–C$_{10}$ alkyl or C$_4$–C$_{20}$ aryl, provided at least one of R$_2$, R$_3$ and R$_4$ is F, fluorinated C$_1$–C$_{10}$ alkyl, fluorinated C$_3$–C$_{10}$ cycloalkyl, or fluorinated C$_4$–C$_{20}$ aryl;
each R$_5$ is independently fluorinated C$_1$–C$_{10}$ alkyl, fluorinated C$_4$–C$_{20}$ aryl, C$_4$–C$_{20}$ aryloxide, fluorinated C$_4$–C$_{20}$ aryloxide, C$_1$–C$_{10}$ alkoxide or fluorinated C$_1$–C$_{10}$ alkoxide;
each of R$_6$ and R$_7$ is independently H or C$_1$–C$_{10}$ alkyl; and
each of a, b and c is independently an integer from 0 to 4, provided the sum of a, b and c is an integer from 2 to 8; and provided that when $R_2$ is a fluorinated $C_1$–$C_4$ alkyl, $R_1$ is a bond, b, and c are 0, and $R_3$ is $C_1$–$C_{10}$ alkyl or fluorinated $C_1$–$C_{10}$ alkyl then $R_4$ is F, fluorinated $C_1$–$C_{10}$ alkyl or fluorinated $C_4$–$C_{20}$ aryl.

2. The compound of claim 1, wherein $M_1$ is selected from the group consisting of Al, B, V, Ti, Si, Zr, Cu, Ge, Sn, Y, Zn, Ga, Nb, Ta, Bi, P, As, Sc, Hf and Sb.

3. The compound of claim 2, wherein $M_1$ is selected from the group consisting of Al, B, Nb and Ta.

4. The compound of claim 3, wherein $M_1$ is selected from the group consisting of Al and B.

5. The compound of claim 1, wherein X is F.

6. The compound of claim 1, wherein $R_5$ is pentafluorophenyl.

7. The compound of claim 1, wherein Z is O and $R_1$ is a bond.

8. The compound of claim 7, wherein $R_2$ is trifluoromethyl, and each of $R_3$ and $R_4$ is independently phenyl or methyl;

$R_2$, $R_3$ and $R_4$ are trifluoromethyl;

$R_2$ is trifluoromethyl, $R_3$ is phenyl, and $R_4$ is phenyl or pentafluorophenyl; or $R_2$ and $R_3$ are phenyl, and $R_4$ is pentafluorophenyl.

9. The compound of claim 1, wherein $R_5$ is 2-trifluoromethyl-phenoxide, 3-trifluoromethylphenoxide, 4-trifluoromethylphenoxide, pentafluorophenoxide, or pentafluorophenyl.

10. The compound of claim 1, wherein the sum of a, b and c is 4.

11. The compound of claim 1, wherein Z is O and $R_1$ is methylene.

12. The compound of claim 11, wherein b and c are 0, a is 4 and $R_2$, $R_3$ and $R_4$ are F.

13. An electrolyte for an electrochemical device comprising the compound of claim 1.

14. The electrolyte of claim 13, wherein the counter cation of said monoanion is lithium.

15. A compound comprising an anion of the formula:

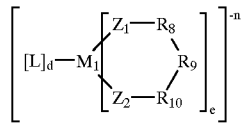

wherein $M_1$ is a transition metal, or a Group III, IV or V element;

L is a halide, $C_1$–$C_{10}$ alkyl, fluorinated $C_1$–$C_{10}$ alkyl, $C_4$–$C_{20}$ aryl, fluorinated $C_4$–$C_{20}$ alkyl or a moiety of the formula —$Z_3$—$R_{11}$;

d is an integer from 0 to 4;

e is an integer from 1 to 3;

the sum of d and e is an integer from 1 to 6;

n is 1 or 2;

each of $Z_1$, $Z_2$ and $Z_3$ is independently O, S, or $NR_6R_7$;

each of $R_6$ and $R_7$ is independently H or $C_1$–$C_{10}$ alkyl;

each $R_9$ is independently $C_1$–$C_{30}$ alkylene, fluorinated $C_1$–$C_{30}$ alkylene, substituted $C_1$–$C_{30}$ alkylene, $C_3$–$C_{10}$ cycloalkylene, fluorinated $C_3$–$C_{10}$ cycloalkylene, $C_4$–$C_{20}$ arylene or fluorinated $C_4$–$C_{20}$ arylene;

each of $R_8$ and $R_{10}$ is a bond, or a moiety of the formula —[C($R_{12}R_{13}$)]$_x$—;

each x is independently an integer from 1 to 4;

each of $R_{12}$ and $R_{13}$ is independently H, F, $C_1$–$C_4$ alkyl or fluorinated $C_1$–$C_4$ alkyl; and each $R_{11}$ is independently $C_1$–$C_{10}$ alkyl, fluorinated $C_1$–$C_{10}$ alkyl, $C_4$–$C_{20}$ aryl, or fluorinated $C_4$–$C_{20}$ aryl;

provided at least one of $R_8$ and $R_{10}$ is a moiety of the formula —C($R_{12}R_{13}$)— and at least one of $R_{12}$ and $R_{13}$ is F or fluorinated $C_1$–$C_4$ alkyl.

16. The compound of claim 15, wherein $M_1$ is selected from the group consisting of Al, B, V, Ti, Si, Zr, Ge, Sn, Cu, Y, Zn, Ga, Nb, Ta, Bi, P, As, Sc, Hf and Sb.

17. The compound of claim 16, wherein $M_1$ is selected from the group consisting of Al, B, Nb and Ta.

18. The compound of claim 17, wherein $M_1$ is selected from the group consisting of Al and B.

19. The compound of claim 15, wherein $R_{12}$ and $R_{13}$ are fluorinated $C_1$–$C_4$ alkyl.

20. The compound of claim 19, wherein $R_{12}$ and $R_{13}$ are trifluoromethyl.

21. The compound of claim 15, wherein the sum of d and e is 2 or 4.

22. The compound of claim 15, wherein n is 1, $Z_1$ and $Z_2$ are O, $R_8$ is a moiety of the formula —C($R_{12}R_{13}$)—, $R_{10}$ is a bond, and $R_{12}$ and $R_{13}$ are trifluoromethyl.

23. The compound of claim 15, wherein n is 1 and the —$Z_1$—$R_8$—$R_9$—$R_{10}$—$Z_2$— moiety comprises:

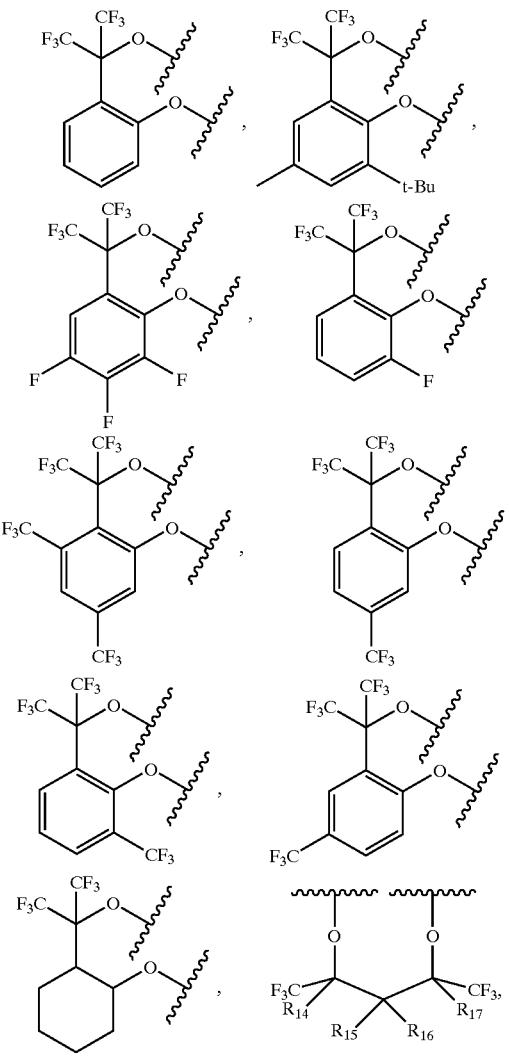

-continued

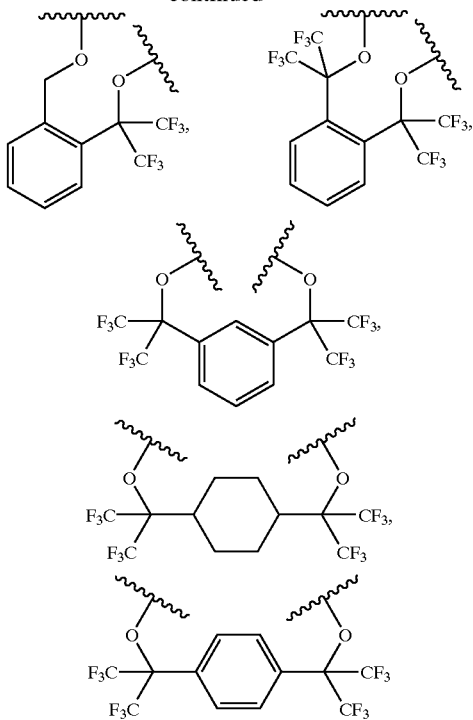
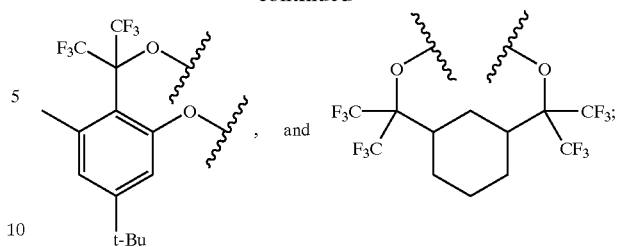

wherein each of $R_{14}$, $R_{15}$, $R_{16}$, and $R_{17}$ is independently H, $C_1-C_{10}$ alkyl, fluorinated $C_1-C_{10}$ alkyl, $C_4-C_{20}$ aryl, or fluorinated $C_4-C_{20}$ aryl.

24. The compound of claim 23, wherein $R_{14}$ and $R_{17}$ are trifluoromethyl, $R_{15}$ is H, and $R_{16}$ is phenyl.

25. The compound of claim 15, wherein d is 0 and e is 2.

26. The compound of claim 15, wherein d is 2 and e is 2.

27. The compound of claim 15, wherein L is F.

28. The compound of claim 15, wherein $R_9$ is $C_4-C_{20}$ arylene or fluorinated $C_4-C_{20}$ arylene.

29. An electrolyte for an electrochemical device comprising a compound of claim 15.

* * * * *

UNITED STATES PATENT AND TRADEMARK OFFICE
CERTIFICATE OF CORRECTION

PATENT NO.       : 6,392,076 B1
APPLICATION NO.  : 09/523502
DATED            : May 21, 2002
INVENTOR(S)      : Steven H. Strauss, Benjamin P. Fauber and Benjamin G. Nolan It is certified that error appears in the above-identified patent and that said Letters Patent is hereby corrected as shown below:

Column 3, line 20, the "$C_4$" should read --$C_1$--.
Column 3, line 35, the "fluorinated $C_1$-$C_{20}$ alkyl" should read --fluorinated $C_4$-$C_{20}$ aryl--.
Column 4, line 26, please delete "," after "b".
Column 4, line 42, the ""fluorinated $C_4$-$C_{20}$ alkyl" should read --fluorinated $C_4$-$C_{20}$ aryl--.
Column 5, line 45, the "cation" should read --cations--.
Column 7, line 27, the "refered" should read --referred--.
Column 7, line 36, the "refered" should read --referred--.
Column 10, line 7, the "-0" should read --~0--.
Column 10, line 53, the "Li" should read --$Li^+$--.
Column 14, line 2, the "$(C_6F_5)$" should read --$(C_6F_5)_3$--.
Column 14, line 17, the "day" should read --days--.
Column 14, line 28, the "δ-72.40" should read --δ -72.40--.
Column 14, line 36, the "day" should read --days--.
Column 14, line 47, the "δ-84.62" should read -- δ -84.62--.
Column 14, line 59, the "δ-76.15" should read -- δ -76.15--.
Column 14, line 65, the "$LiOH.H_2O$" should read --$LiOH•H_2O$--.
Column 15, line 10, the "δ-75.00" should read --δ -75.00--.
Column 15, line 17, the "$LiOH.H_2O$" should read --$LiOH•H_2O$--.
Column 15, line 31, the "δ-72.81" should read --δ -72.81--.
Column 15, line 37, the "$LiOH.H_2O$" should read --$LiOH•H_2O$--.
Column 15, line 49, the "δ-75.42" should read --δ -75.42--.
Column 16, line 19, the "D6" should read --$D_6$--.
Column 16, line 19, the "δ-72.47" should read --δ -72.47--.
Column 17, line 51, the "fluorinated $C_4$-$C_{20}$ alkyl" should read --fluorinated $C_4$-$C_{20}$ aryl--.

Signed and Sealed this

Thirty-first Day of July, 2007

JON W. DUDAS
*Director of the United States Patent and Trademark Office*